United States Patent
Jones, Jr. et al.

(10) Patent No.: US 10,259,813 B2
(45) Date of Patent: Apr. 16, 2019

(54) COMPOSITIONS COMPRISING FOLIC ACID DERIVATIVES, THEIR PREPARATIONS AND METHODS OF USE

(71) Applicant: Chemic Laboratories, Inc., Canton, MA (US)

(72) Inventors: Gerald S. Jones, Jr., Norwood, MA (US); Joseph P. St. Laurent, Lakeville, MA (US); Scott A. Goodrich, Stoughton, MA (US)

(73) Assignee: Chemic Laboratories, Inc., Canton, MA (US)

( * ) Notice: Subject to any disclaimer, the term of this patent is extended or adjusted under 35 U.S.C. 154(b) by 0 days.

(21) Appl. No.: 15/912,070

(22) Filed: Mar. 5, 2018

(65) Prior Publication Data

US 2019/0048011 A1   Feb. 14, 2019

Related U.S. Application Data

(63) Continuation of application No. 15/173,164, filed on Jun. 3, 2016, now Pat. No. 9,938,280, which is a continuation of application No. 14/417,504, filed as application No. PCT/US2013/052304 on Jul. 26, 2016, now Pat. No. 9,382,251.

(60) Provisional application No. 61/676,651, filed on Jul. 27, 2012.

(51) Int. Cl.
C07D 475/04    (2006.01)
C07D 487/14    (2006.01)
A61K 31/519    (2006.01)

(52) U.S. Cl.
CPC .......... *C07D 475/04* (2013.01); *A61K 31/519* (2013.01); *C07D 487/14* (2013.01)

(58) Field of Classification Search
CPC ... C07D 475/04; C07D 487/14; A61K 31/519
See application file for complete search history.

(56) References Cited

PUBLICATIONS

Tyagi, et al., Thermal Degradation of (6R,S)-5,10-methenyltetrahydrofolate in aqueous solution at pH 8, Chemical Physics 358, 132-136 (2009). (Year: 2009).*

* cited by examiner

*Primary Examiner* — Erich A Leeser
(74) *Attorney, Agent, or Firm* — Goodwin Procter LLP

(57) ABSTRACT

Described herein are methods for making folic acid derivatives, intermediates, pharmaceutical compositions and uses thereof.

14 Claims, No Drawings

COMPOSITIONS COMPRISING FOLIC ACID DERIVATIVES, THEIR PREPARATIONS AND METHODS OF USE

CROSS-REFERENCE AND CLAIM OF PRIORITY

This application is a continuation of U.S. Ser. No. 15/173,164, filed Jun. 3, 2016, which is a continuation of U.S. Ser. No. 14/417,504, filed Jul. 26, 2013, which is a National Stage Application under 35 U.S.C. § 371 of International Application No. PCT/US2013/052304, filed Jul. 26, 2013, which claims priority to U.S. Ser. No. 61/676,651, filed Jul. 27, 2012, the contents of each of which is hereby incorporated by reference in its entirety.

BACKGROUND OF INVENTION

Folic acid (FA), also known as pteroyl-L-glutamic acid, is a vital co-factor in enzymatic reactions necessary for the synthesis of nucleic acids, amino acids, and other biological molecules. Although many organisms are capable of synthesizing folic acid, humans are unable to synthesize folic acid, and must depend on adequate dietary intake of this essential nutrient.

Without adequate intake of folic acid, humans may develop a folate deficiency. Folate deficiency has several negative impacts on the human body, including but not limited to: (i) the defective maturation of different cell types; (ii) nervous system disorders; (iii) a decreased immune response; and (iv) the development of peripheral vascular disease. It has also been found that insufficient folate levels during pregnancy correlate with the occurrence of neural tube defects in newborns. Low folate levels may also lead to megaloblastic anemia, a disorder which results in inadequate production of red blood cells, particularly during pregnancy and in geriatrics.

The clear connection between adequate folate intake and health has resulted in the establishment of a recommended dietary allowance (RDA) for folic acid by the U.S. government. Although folic acid is currently added to all commercial over the counter (OTC) vitamin preparations, and to some foods, folic acid is not the primary form of folate which is found naturally in fresh foods. More commonly, the primary forms of folate which are found in natural fresh foods are polyglutamates. Of these polyglutamates, the polyglutamate forms of (6S)-methylTHFA (e.g., the compound of formula (I) where $R^1$ is $NH_2$, $R^2$ is OH and $R^3$ is H) and (6S)-5-formylTHFA predominate. However, since the primary form of folate which can be absorbed by the human body bears only a single glutamic acid residue, polyglutamates, after ingestion, must be processed enzymatically in the digestive tract prior to absorption. Another difference between folic acid and natural folates (e.g. polyglutamates) is that the folates in fresh, uncooked foods are usually present as a reduced form. One example of a reduced folate is tetrahydrofolic acid (THFA) and its derivatives.

There is a reason to believe that in a segment of the population the absorption of reduced folates, such as tetrahydrofolic acid (THFA), may exceed folic acid, resulting in greater bioavailability. Thus, dietary, supplementation with these reduced folates (e.g., THFA) may constitute an improved method for meeting the RDA of folic acid. In fact, the calcium salt of (6S)-methylfolate (Formula (I); X=Ca), also known as, L-methylfolate, is currently commercially available under the trade name Metafolin™ for use as a dietary supplement. In addition to the foregoing, (6S)-5-methylfolate may be the body's preferred form of folate, since it is the predominant form of folate found in humans.

Although the importance of folic acid in the diet has been recognized, prior and widespread use of reduced folates as dietary supplements has been limited, in part by the stereochemistry of these compounds. The chemical structure of folic acid contains a single chiral center in the glutamic acid portion of the molecules (see formula (I), where the chiral center is denoted by an asterisk). Reduction of folic acid to THFA creates a second chiral center at the 6-position of the pteridine nucleus. When the reduction of folic acid is carried out chemically, a mixture of two isomers called diastereomers (or more appropriately, epimers) results, whereby the orientation of substituents at the 6-position in each isomer is different. Each of these distinct orientations, or configurations, is designated as either S or R in accordance with the Cahn-Ingold-Prelog convention. As a result of the aforementioned reduction of folic acid, one-half of the molecules have the S-configuration at the 6-position, and one-half of the molecules have the R-configuration at the 6-position. Conversely, reduction of folic acid enzymatically, e.g., by the enzyme dihydrofolate reductase (DHFR), proceeds stereoselectively, and results in only the production of (6S)-THFA. It is important to note that all tetrahydrofolates that occur naturally are found in only one diasterereomeric form, i.e., the absolute configuration at the 6-position is either S or R. Accordingly, the S designation is assigned to (i) naturally-occurring THFA, (ii) 5-methylTHFA, and (iii) 5-formylTHFA, whereas the R designation is assigned to (i) naturally-occurring 5,10-methyleneTHFA, and (ii) 10-formylTHFA.

In addition to the naturally occurring diastereomeric forms of reduced folates, it has been found that some unnatural isomers of reduced folates (i.e., those in which the configuration at the 6-position is opposite that of natural isomers) can exhibit considerable absorption in the human gastrointestinal (GI) tract. However, a low order of biological activity has been ascribed to the unnatural isomers and, more importantly, it appears that the unnatural isomers may have an inhibitory effect upon certain enzymatic processes. Due to these factors, and because the effect of chronic or long-term exposure to these unnatural isomers is unknown, there has been a recent trend to use only diastereomerically pure (or natural) (6S)-isomers of reduced folates as therapeutic agents, e.g., (6S)-5-formylTHFA or calcium leucovorin, and dietary supplements (e.g., Metafolin™).

A variety of methods are currently available for the production of these desirable pure folate isomers. At present, the methods which are used for commercial production of folate isomers rely on the resolution of pairs of diastereomers, particularly by fractional crystallization/recrystallization techniques. For example, Metafolin™ is produced by such a method. Some of these methods produce large volumes of undesirable by-products which need to be removed, and thus negatively influence the economy and efficiency of the process. Others of these methods require multiple fractionations/recrystallizations to achieve a product of high diastereomeric excess, and therefore can be time-consuming and costly.

In addition to the foregoing, there is an approach which uses the chromatographic separation of diastereomers, but it does not lend itself to large-scale production of pure folate isomers. Furthermore, there is a method which synthesizes (6S)-THFA via the stereoselective catalytic hydrogenation of dihydrofolic acid (DHFA), but the cost of the exotic organometallic catalyst(s) is prohibitive for large-scale production. A chemoenzymatic method has also been described for producing small quantities of (6S)-THFA and derivatives, but this latter method is typically regarded as unsuitable for commercial application due to its complexity (Tetrahedron 1986, 42, 117-136).

Thus, a need remains for providing a cost-effective, large-scale synthesis for producing L-methylfolate.

SUMMARY OF INVENTION

Disclosed herein are compositions (e.g., oral dosage forms and vitamin supplements) of a compound of formula (V), methods of making a compound of formula (V) and methods of making a compound of formula (I).

In one aspect, the present invention is directed to a composition (e.g., a pharmaceutical composition) of a compound of formula (V):

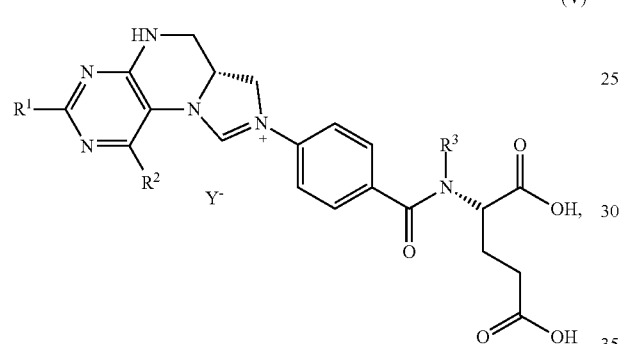

wherein, $R^1$ and $R^2$ are each independently selected from H, OH, $NH_2$, $C_{1-6}$ alkyl or aryl;

$R^3$ is H, $C_{1-6}$ alkyl or aryl; and

Y is halo.

In some embodiments, $R^1$ is $NH_2$. In some embodiments, $R^2$ is OH. In some embodiments, $R^3$ is H. In some embodiments, $R^1$ is $NH_2$, $R^2$ is OH and $R^3$ is H.

In some embodiments, Y is chloro.

In another aspect, the present invention is directed to an oral dosage form comprising a compound of formula (V).

In another aspect, the present invention is directed to a dietary supplement comprising a compound of formula (V). In some embodiments, the dietary supplement is a prenatal vitamin comprising a compound of formula (V). In embodiments, when a composition or oral dosage form comprising a compound of formula (V) is administered to a subject, the compound of formula (V) converts in vivo to a bioavailable form of folate.

In some embodiments, the dietary supplement further comprises one or more vitamins (e.g., vitamin A, C, B-12 or D).

In some embodiments, the composition, oral dosage form or dietary supplement is substantially free of any compounds of formula (I), (II) or (III):

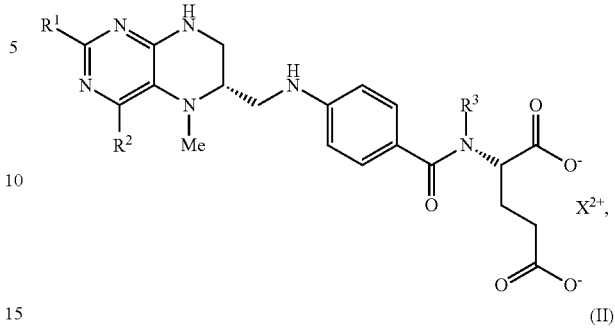

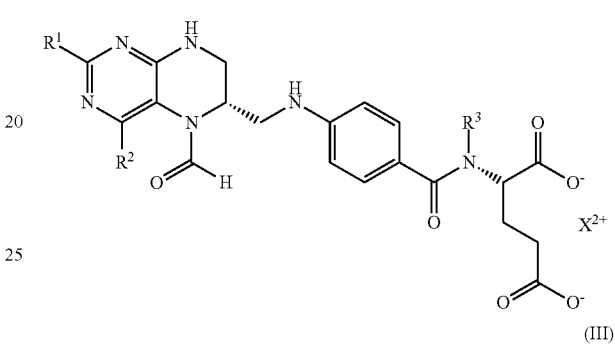

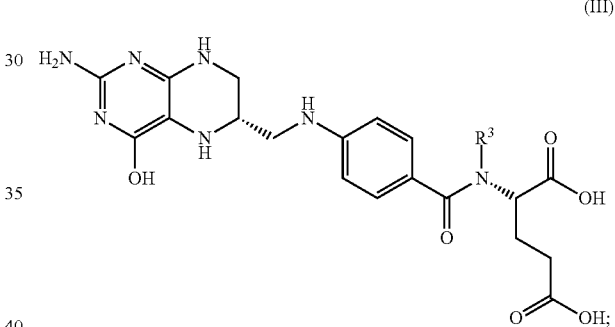

wherein each of $R^1$, $R^2$, $R^3$, and X are defined as in formula (V). In some embodiments, the composition of formula (V) is substantially free of solvent, e.g., water or ethanol.

In another aspect, the present invention is directed to a method for making a compound of formula (V), the method comprising converting a compound of formula (II) into a compound of formula (V), for example, by cyclization of the compound of formula (II) to form a compound of formula (V):

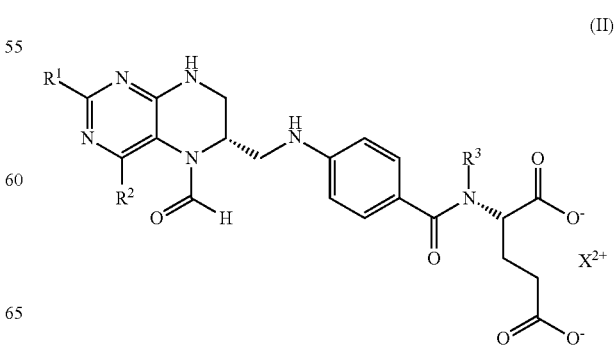

-continued

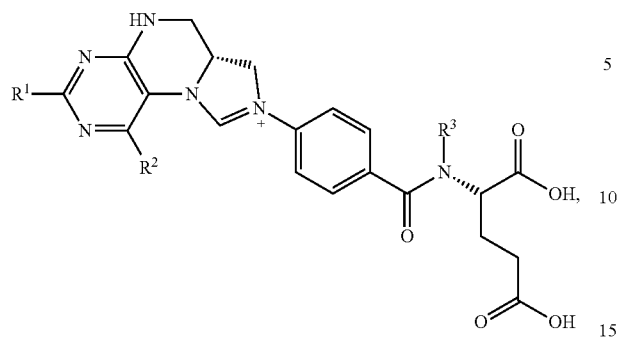

wherein,
R¹ and R² are each independently selected from H, OH, NH₂, C₁₋₆ alkyl or aryl;
R³ is H, C₁₋₆ alkyl or aryl; and
X is Na, K, Mg or Ca.

In certain embodiments, the cyclization step is carried out in the presence of an acid such as formic acid. In some embodiments, the cyclization step is carried out in the presence of a strong acid (e.g., an aqueous HCl solution). In some embodiments, the cyclization is carried out in the presence of a mixture of formic and hydrochloric acid. In some embodiments, the cyclization step comprises a solvent (e.g., an aqueous solvent). The reaction can be performed under ambient conditions, for example, room temperature and atmospheric pressure.

In some embodiments, the method comprises isolation of the compound of formula (V), for example, by filtration.

In some embodiments, the compound of formula (V) is further converted to a compound of formula (I)

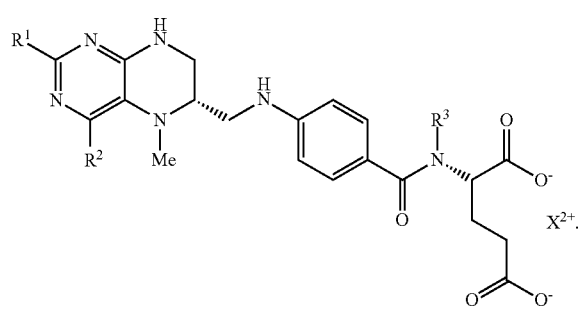

The compound of formula (V) can be converted into a compound of formula (I) by subjecting the compound of formula (V) to a reducing agent, for example, a hydride such as NaBH₄. In some embodiments, the reducing agent is in a basic solution such as a NaOH solution. In some embodiments, the method further comprises subjecting the reaction mixture of a sale such as a Ca salt (e.g., CaCl₂).

In certain embodiments, R¹ is NH₂. In some embodiments, R² is OH. In some embodiments, R³ is H. In some embodiments, R¹ is NH₂, R² is OH and R³ is H. In some embodiments, R¹ is NH₂, R² is OH and R³ is H.

In some embodiments, X is Ca.

In another aspect, the invention is directed to a method for making a compound of formula (I):

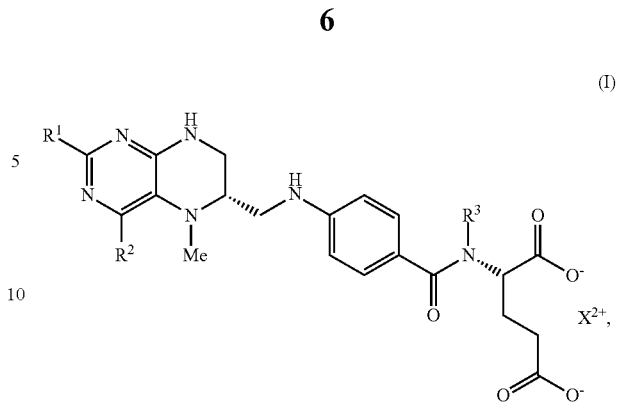

the method comprising a reduction of a compound of formula (V) as defined above, to make a compound of formula (I),

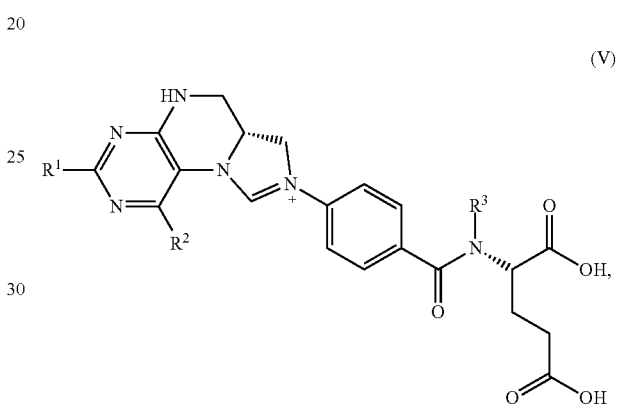

wherein
R¹ and R² are each independently selected from H, OH, NH₂, C₁₋₆ alkyl or aryl;
R³ is H, C₁₋₆ alkyl or aryl;
Y is halo; and
X is Na, K, Mg or Ca.

In certain embodiments, the reduction of a compound of formula (V) is carried out in the presence of a reducing agent (e.g., sodium borohydride). In some embodiments, the reduction step further comprises a strong base (e.g., sodium hydroxide). In some embodiments, the reduction step is carried out in the presence of a solvent (e.g., an aqueous solvent).

In certain embodiments, R¹ is NH₂. In some embodiments, R² is OH. In some embodiments, R³ is H. In some embodiments, R¹ is NH₂, R² is OH and R³ is H. In some embodiments, X is Ca.

In some embodiments, the method further comprises converting a compound of formula (II) to a compound of formula (V), for example, using a method described above.

In certain embodiments, the methods described herein are carried out on at least 50 g of the starting material. In some embodiments, the methods described herein are carried out on at least 100 g of the starting material. In some embodiments, the methods described herein are carried out on at least 250 g of the starting material. In some embodiments, the methods described herein are carried out on at least 400 g of the starting material. In some embodiments, the methods described herein are carried out on at least 500 g of the starting material. In some embodiments, the methods described herein are carried out on at least 1 kg of the starting material. In some embodiments, a method described herein is performed as a batch process.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various isomeric forms, e.g., stereoisomers and/or diastereomers. Thus, compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of stereoisomers or diastereomers are provided.

Where a particular enantiomer or diastereomer is preferred, it may, in some embodiments be provided substantially free of the corresponding enantiomer and/or diastereomers, and may also be referred to as "optically enriched." "Optically-enriched," as used herein, means that the compound is made up of a significantly greater proportion of one enantiomer or diastereomer. In certain embodiments the compound is made up of at least about 90% by weight of a preferred enantiomer or diastereomer. In other embodiments the compound is made up of at least about 95%, 98%, or 99% by weight of a preferred enantiomer or diastereomer. Preferred enantiomers or diastereomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The compounds of this invention may contain one or more asymmetric centers and thus occur as racemates and racemic mixtures, single enantiomers, individual diastereomers and diastereomeric mixtures. Described herein are enantiomerically enriched compounds (e.g., a compound resolved to an enantiomeric excess of 60%, 70%, 80%, 85%, 90%, 95%, 99% or greater). All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts. For example a compound can be resolved to an enantiomeric excess (e.g., 60%, 70%, 80%, 85%, 90%, 95%, 99% or greater) via formation of diastereomeric salts, e.g. with a chiral base, e.g., (+) or (−) α-methylbenzylamine, or via high performance liquid chromatography using a chiral column. In some embodiments a product is purified directly on a chiral column to provide enantiomerically enriched compound.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer. ee=(90-10)/100=80%. Thus, a composition containing 90% of one enantiomer and 10% of the other enantiomer is said to have an enantiomeric excess of 80%.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O—), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

DETAILED DESCRIPTION

Compositions and Oral Dosage Forms

The present invention also features compositions such as pharmaceutical compositions, dietary supplements, and oral dosage forms of a compound of formula (V), either alone or in combination, together with a suitable excipient. In some preferred embodiments, the composition (e.g., pharmaceutical composition or dietary supplement) is a composition that can be administered to a subject orally, e.g., a liquid composition such as a solution. In some embodiments, the composition is a solid composition, for example, a lyophilite, which can be further processed prior to administering the composition to a subject, for example, the solid composition can be further processed to form a liquid composition such as a solution.

The pharmaceutical compositions of this invention may be administered orally. Compositions suitable for oral administration may be in the form of capsules, cachets, pills, tablets, lozenges (using a flavored base, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres.

In some embodiments, the compound of formula (V) is administered with one or more additional agents such as vitamins or other dietary supplements.

Methods of Use

Folic acid and derivatives thereof can be found in found in naturally fresh foods. In certain embodiments, a compound of formula (V) may serve as biological precursors to folic acid, e.g., a bioavailable precursor to folic acid. In certain other embodiments, a compound of formula (V) may be used as a dietary supplement. Compositions and oral dosage forms of the compound of formula (V) can be administered to a subject in need of folic acid, for example a pregnant female.

Methods of Making Compounds as Described Herein

The compounds of formula (I) and (V) described herein can be made using a variety of synthetic techniques.

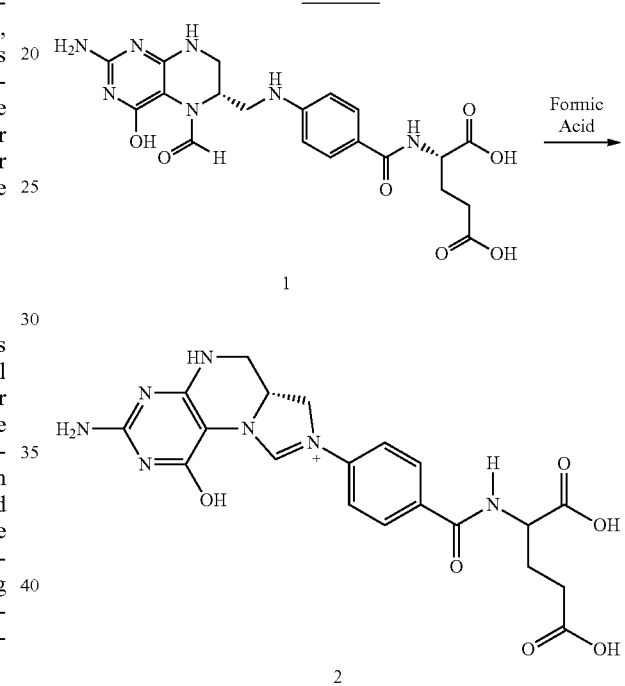

Scheme 1 above is an exemplary synthetic scheme that depicts a representative synthesis of compounds of formula (V) described herein. Calcium leucovorin 1 is reacted with formic acid to produce tricycle 2 also referred to as ALV. Compounds of formula (V) can also be produced using a variety of synthetic techniques.

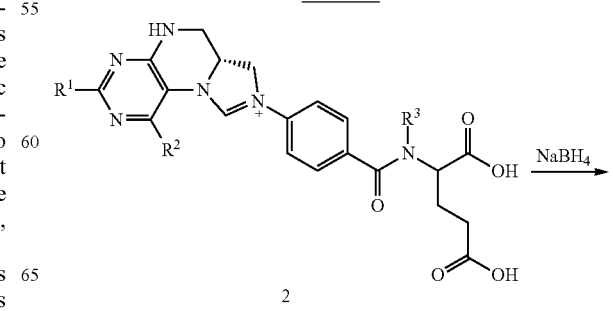

-continued

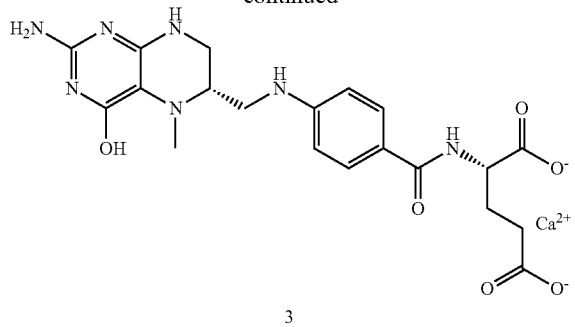

3

Scheme 2 above is an exemplary synthetic scheme that depicts a representative synthesis of compounds of formula (I) described herein. ALV 2 is treated with sodium borohydride to produce compound 3. Compounds of formula (I) can also be produced using a variety of acceptable synthetic techniques.

In embodiments, the methods described herein can be used to produce an enantiomerically enriched product.

Reaction Mixtures

The present invention also refers to a reaction mixture comprising a compound of formulas (II), (V) or (I), e.g., a reaction mixture that is present during a method or process described herein.

In certain embodiments, the methods or reaction mixtures described herein further comprise a solvent. In certain embodiments, the solvent is an aqueous solvent (e.g., water). In certain embodiments, the solvent is an organic solvent. In certain embodiments, the solvent is an aprotic solvent. Exemplary organic solvents include, but are not limited to, benzene, toluene, xylenes, methanol, ethanol, isopropanol, acetonitrile, acetone, ethyl acetate, ethyl ether, tetrahydrofuran, methylene chloride, carbon tetrachloride, N-methylpyrrolidinone (NMP), N-methylmorpholine (NMM), dichloroethane and chloroform, or a mixture thereof.

In certain embodiments, the reaction is carried out below room temperature, e.g., a cooled reaction such as a reaction at a temperature of 0° C. or lower. In certain embodiments, the reaction is carried out above room temperature, e.g., by heating, e.g., from 25° C.-40° C. In certain embodiments, the reaction occurs under an inert atmosphere, e.g., an atmosphere of an inert gas such as nitrogen or argon. In certain embodiments, the reaction takes place under anhydrous conditions, e.g., conditions that are substantially free of water.

In some embodiments, the compounds described herein are in a reaction mixture comprising a solvent, e.g., as a mixture such as a solution or a heterogeneous mixture. The reaction mixture can be free of compounds that would react with or degrade a compound described herein e.g., the reaction mixture can be substantially free of water and/or substantially free of any reactive gases.

INCORPORATION BY REFERENCE

All publications and patents mentioned herein are hereby incorporated by reference in their entirety as if each individual publication or patent was specifically and individually indicated to be incorporated by reference.

EXAMPLES

General Experimental Procedures

Example 1

Preparation of Tricycle (4) from Calcium Leucovorin (6)

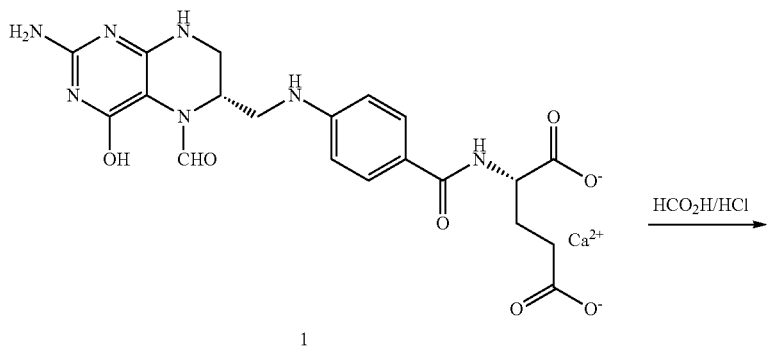

1

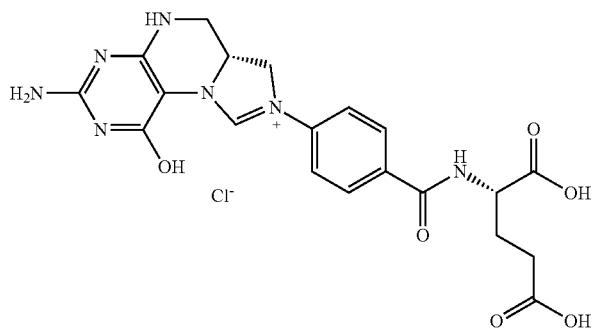

2

A 30 L jacketed reactor was fitted with a complete stir shaft assembly and thermocouple. The reactor was charged with HCOOH (88%, 14.3 L), followed by conc HCl (2.5 L), and then water (1103 mL). Calcium leucovorin (1; 3942 g) was added to the reactor with stirring, followed by additional HCOOH (990 mL). After stirring for 17 h at ambient temperature, crude 2 was collected by vacuum filtration, and washed with EtOH (3×8 L). The damp filter cake was dried under vacuum at 75° C. to a constant weight. Yield: ~2,740 g.

Example 2

Conversion of Anhydroleucovorin (2) to Calcium Salt of (6S)-methylfolate (3)

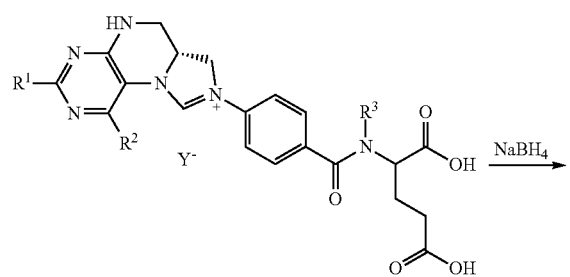

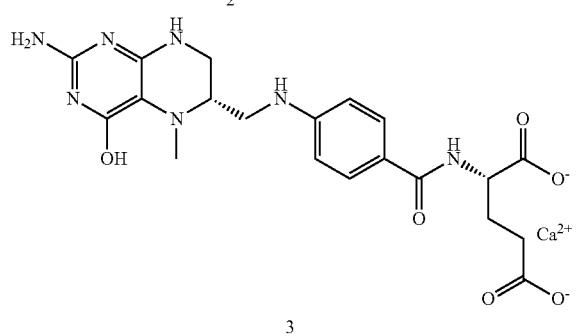

A 30 L jacketed reactor was fitted with a complete stir shaft assembly, thermocouple and heated/refrigerated recirculator. Water (15 L) and sodium hydroxide pellets (254 g) were added to the reactor and allowed to mix until dissolved. Sodium borohydride (1046 g) was added and allowed to mix until dissolved. The reactor was cooled to <8° C. and anhydroleucovorin (2, 3300 g) was slowly added over ~1-3 hours. The contents of the reactor were allowed to mix for 1 hour at room temperature and then sodium borohydride (231 g) was slowly added. The contents of the reactor were allowed to mix for 1 hour at room temperature and then sodium borohydride (114 g) was very slowly added. The contents of the reactor were allowed to mix for one hour at room temperature. The borate salts byproducts were isolated by vacuum filtration and washed with water (1.5 L). The reactor was rinsed with water to remove residual salts. The filtered solution was added to the reactor and pH adjusted to 7.0-7.4 by slowly adding concentrated hydrochloric acid (37%, ~330 mL). An aqueous solution of calcium chloride (19%, 5300 g) was slowly added over ~10-30 minutes to effect precipitation. The contents of the reactor were cooled to 0-8° C. and allowed to mix 12-16 hours. The crude 3 was collected by vacuum filtration and washed with water (3 L) followed by methanol (3 L). The damp filter cake was added to the reactor, reslurried in methanol (30 L) for 2 hours at room temperature, filtered and washed with methanol (5 L). The damp filter cake was added to the reactor, refluxed in methanol (30 L) for 2 hours, filtered warm and washed with methanol (5 L). The methanol reflux procedure was repeated. The isolated solids were dried invacuo at 60° C. to a constant weight. Yield ~2,300 g.

What is claimed is:

1. A method of treating a folic acid deficiency in a subject in need thereof, comprising administering to the subject an oral dosage form comprising a compound of Formula (V):

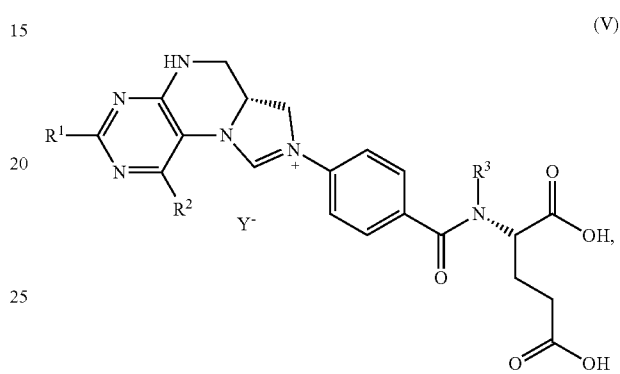

wherein
$R^1$ and $R^2$ are each independently selected from H, OH, $NH_2$, $C_{1-6}$ alkyl or aryl;
$R^3$ is H, $C_{1-6}$ alkyl or aryl; and
Y is halo.

2. The method of claim 1, wherein $R^1$ is $NH_2$.
3. The method of claim 1, wherein $R^2$ is OH.
4. The method of claim 1, wherein $R^3$ is H.
5. The method of claim 1, wherein Y is Cl.
6. The method of claim 1, wherein $R^1$ is $NH_2$, $R^2$ is OH and $R^3$ is H.
7. The method of claim 1, wherein the subject is a pregnant female.
8. A method of providing folic acid to a subject in need thereof, comprising administering to the subject an oral dosage form comprising a compound of Formula (V):

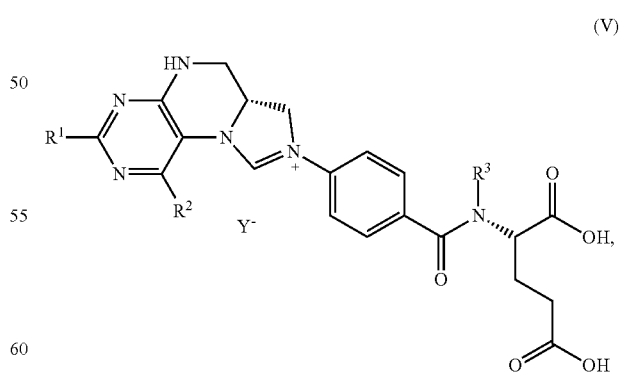

wherein
$R^1$ and $R^2$ are each independently selected from H, OH, $NH_2$, $C_{1-6}$ alkyl or aryl;
$R^3$ is H, $C_{1-6}$ alkyl or aryl; and
Y is halo.

9. The method of claim 8, wherein $R^1$ is $NH_2$.
10. The method of claim 8, wherein $R^2$ is OH.
11. The method of claim 8, wherein $R^3$ is H.
12. The method of claim 8, wherein Y is Cl.
13. The method of claim 8, wherein $R^1$ is $NH_2$, $R^2$ is OH and $R^3$ is H.
14. The method of claim 8, wherein the subject is a pregnant female.

* * * * *